United States Patent [19]
Springer et al.

[11] Patent Number: 6,004,550
[45] Date of Patent: *Dec. 21, 1999

[54] INTRACELLULAR EXPRESSION OF CARBOXYPEPTIDASE G2 IN A NITROGEN MUSTARD PRODRUG SYSTEM

[75] Inventors: Caroline Joy Springer, Sutton; Richard Marais, London, both of United Kingdom

[73] Assignee: Cancer Research Campaign Technology Limited, London, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/776,246

[22] PCT Filed: Jul. 27, 1995

[86] PCT No.: PCT/GB95/01783

§ 371 Date: Jan. 30, 1997

§ 102(e) Date: Jan. 30, 1997

[87] PCT Pub. No.: WO96/03151

PCT Pub. Date: Feb. 8, 1996

[30] Foreign Application Priority Data

Jul. 27, 1994 [GB] United Kingdom .................. 9415167

[51] Int. Cl.$^6$ .......................... A61K 48/00; C12N 15/00; C12Q 1/00

[52] U.S. Cl. ........................ 424/93.21; 424/93.2; 435/29; 435/320.1; 435/325; 435/357

[58] Field of Search .............................. 514/44; 424/93.1, 424/93.2, 93.21; 435/320.1, 29, 325, 357; 536/23.1, 24.1

[56] References Cited

U.S. PATENT DOCUMENTS 5,665,543  9/1997  Foulkes et al. ............................. 435/6

FOREIGN PATENT DOCUMENTS

A0415731  3/1991  European Pat. Off. .
WO94/02450  2/1994  WIPO .

OTHER PUBLICATIONS (Mullen (1994) Pharm. Ther. 63, 199–207, 1994.
Cornell et al (1976) Biotech.Bioeng. vol. XVIII, 1171–1174, 1976.
Yasuda et al (1994) Bull. Mukogawa Univ. Nat. Sci. 42, 63–66, 1994.
Mullen (1994) Pharmac. Therap. 63, 199–207.
Ann. N.Y., Acad. Sci., vol. 716, May 31, 1994 pp. 115–125, K. Sikora et al, "Therapeutic strategies using c–34bB–2 promoter–controlled drug activation".
Trends in Biotechnology, vo. 11, No. 5, 3, Cambridge GB, pp. 197–201, K. Sikora, "Gene therapy for cancer".

*Primary Examiner*—Deborah Crouch
*Attorney, Agent, or Firm*—Nixon & Vanderhye P.C.

[57] ABSTRACT

The invention provides a two component system for gene-directed enzyme prodrug therapy which comprises: (a) a vector which encodes a carboxypeptidase which is expressed within a cell; and (b) a prodrug which can be converted into an active drug by said carboxypeptidase, useful in the treatment of tumours.

10 Claims, 3 Drawing Sheets

INTRACELLULAR EXPRESSION OF CARBOXYPEPTIDASE G2 IN A NITROGEN MUSTARD PRODRUG SYSTEM

The present invention relates to gene directed enzyme prodrug therapy (GDEPT) and its use in the treatment of disease, including tumours.

A therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, in order that a prodrug is converted to an active drug within the tumour cells (Huber et al, Proc. Natl. Acad. Sci. USA (1991) 88, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French Anderson, Annu. Rev. Biochem., 1993,62;191. The term "GDEPT" (gene-directed enzyme prodrug therapy) is used to include both viral and non-viral delivery systems.

A number of different enzymes have been proposed as being suitable for use in GDEPT therapy. In general, the enzymes have been selected to be compatible with prodrugs which are known to be effective against the tumour type being treated. It is also important for the success of GDEPT that the drug is capable of entering the cell.

The enzyme carboxypeptidase G2 (CPG2) has been proposed for use in Antibody-Directed Enzyme Prodrug Therapy (ADEPT) systems, in combination with a number of types of prodrugs, including nitrogen mustard prodrugs. In ADEPT, the prodrug is activated outside the cell or on the cell surface, and thus the prodrug was believed to have no significant ability to enter the cell. Also the prodrug contains the hydrophilic glutamic acid. It has now surprisingly been found that such prodrugs not only enter the cell but can be activated intracellularly by CPG2. Furthermore, following activation in the cell, the drugs exhibit an effective bystander effect where surrounding cells are also killed by activated drug.

DISCLOSURE OF THE INVENTION

In order to overcome these problems, the present invention thus provides a two component system for gene-directed enzyme prodrug therapy which comprises: (a) a vector which encodes a carboxypeptidase which is expressed within a cell; and (b) a prodrug which can be converted into an active drug by said carboxypeptidase. The enzyme is preferably a bacterial carboxypeptidase, especially carboxypeptidase CPG2 (SEQ ID No. 1) or Pseudomonas γ-glutamylhydrolase EC3.4.22.12 (Levy CC & Goldman P J. Biol. Chem. 242; p2933 (1967).

The vector may be a RNA or DNA vector. It may be derived from a viral vector, including any suitable vector available in the art for targeting tumour cells.

The invention also provides the system of the invention for use in a method of treatment of a patient, and a method of treating a tumour in a patient in need of treatment which comprises administering to said pat,ient an effective amount of a vector encoding a carboxypeptidase and a prodrug capable of being converted by said enzyme to an active drug.

BRIEF DESCRIPTION OF THE DRAWINGS

FIG. 1 (A–B) Expression of CPG2* in NIH3T3 cells (A) Immunoblot analysis. NIH3T3 cells were transfected with MLVβplink (lane 1) or with MLVCPG2* (lane 2). The cells were extracted into buffer A and samples of each were electrophoresed in 10% w/v polyacrylamide gels, transferred to nitrocellulose and probed with a CPG2 specific polyclonal antibody. The position of migration of CPG2* is shown and the positions of migration of standard molecular mass markers (in kDa) are shown to the left of the figure. (B) CPG2 enzyme activity assay. The cell extracts from part (A) were analysed by CPG2 enzyme activity assay. Sample numbers correspond to lane numbers from part (A). The enzyme activity is expressed in arbitrary units, relative to buffer controls.

DETAILED DESCRIPTION OF THE INVENTION

A. Vector systems

Examples of suitable vector systems include vectors based on the Molony murine leukaemia virus are known (Ram, Z et al, Cancer Research (1993) 53;83–88; Dalton & Treisman, Cell (1992) 68; 597–612). These vectors contain the Murine Leukaemia virus (MLV) enhancer cloned upstream at a β-globin minimal promoter. The β-globin 5' untranslated region up to the initiation ATG is supplied to direct efficient translation of the cloned protein. The initiator ATG straddles an NcoI restriction site and thus can be used to clone a protein coding sequence into the vector. This vector further contains a polylinker to facilitate cloning, followed by the β-globin 3'-untranslated region and polyadenylation sites. The MLV enhancer is of particular use since it is a strong enhancer and is active in most murine and human cell lines.

Suitable viral vectors further include those which are based upon a retrovirus. Such vectors are widely available in the art. Huber et al (ibid) report the use of amphotropic retroviruses for the transformation of hepatoma, breast, colon or skin cells. Culver et al (Science (1992) 256; 1550–1552) also describe the use of retroviral vectors in GDEPT. Such vectors or vectors derived from such vectors may also be used. Other retroviruses may also be used to make vectors suitable for use in the present invention. Such retroviruses include rous sarcoma virus (RSV). The promoters from such viruses may be used in vectors in a manner analogous to that described above for MLV.

Englehardt et al (Nature Genetics (1993) 4; 27–34) describe the use of adenovirus based vectors in the delivery of the cystic fibrosis transmembrane conductance product (CFTR) into cells, and such adenovirus based vectors may also be used. Vectors utilising adenovirus promoter and other control sequences may be of use in delivering a system according to the invention to cells in the lung, and hence useful in treating lung tumours.

Vectors encoding carboxypeptidase may be made using recombinant DNA techniques known per se in the art. The sequences encoding the enzyme may be constructed by splicing synthetic or recombinant nucleic acid sequences together, or modifying existing sequences by techniques such as site directed mutagenesis. Reference may be made to "Molecular Cloning" by Sambrook et al (1989, Cold Spring Harbor) for discussion of standard recombinant DNA techniques. In general, the vector may be any DNA or RNA vector used in VDEPT or GDEPT therapies.

B. Carboxypeptidase

The carboxypeptidase will usually convert the prodrug into an active drug by removing a protecting group from the prodrug. In most cases, the protecting group will be cleaved as a whole from the prodrug. However, it is also possible for the enzyme to cleave or simply alter part of the protecting group, resulting in a partially cleaved or altered protecting group which is unstable, resulting in spontaneous removal of the remainder of the group.

Carboxypeptidase G2 (CPG2) is disclosed in WO88/07378, and its sequence is also set out below as Seq. ID No. 1. Although the CPG2 with the amino acid sequence of Seq. ID No. 1 is preferred, alterations to the sequence which are amino acid substitutions, deletions or insertions (eg. of about 1, 2, 3, 4, 5, 10 or 20 residues in each case) are also possible. In any event, the alteration will be such that the enzyme retains its ability to convert a prodrug to an active drug at substantially the same rate as the native enzyme. In this context, "substantially the same rate" will desirably be within 1 order of magnitude, and preferably from about 50-fold e.g. about 2-fold less to 2, 5 or 10 fold more.

In addition to specific changes the enzyme may otherwise be altered by truncation, substitution, deletion or insertion as long as the activity of the enzyme is substantially unchanged as defined above. For example, small truncations in the N- and/or C-terminal sequence may occur as a result of the manipulations required to produce a vector in which a nucleic acid sequence encoding the enzyme is linked to a suitable promoter. The activity of the altered enzyme may be measured in model systems such as those described in the examples.

An example of a trancated enzyme is CPG2* which contains amino acids 23 to 415 of Seq. ID No. 1.

C. Promoters

The carboxypeptidase will be expressed in the vector using a promoter capable of being expressed in the cell to which the vector is targeted. The promoter will be operably linked to the sequences encoding the enzyme and its associated sequences. For example, the c-erbB2 proto-oncogene is expressed in breast tissues at low levels and in a tissue restricted manner. In some tumour states however the expression of this protein is increased, due to enhanced transcriptional activity. Notable examples of this are breast tissue (about 30% of tumours), ovarian (about 20%) and pancreatic tumours (about 50–75%). In such tumours where expression of c-erbB2 is increased due to enhanced transcription or translation, the c-erbB2 promoter may be used to direct expression of proteins in a cell specific manner.

With the GDEPT system of the present invention utilising c-erbB2 promoters to target such tumours, the specificity of GDEPT is increased since transfection of normal cells by a vector with a c-erbB2 promoter will provide only very limited amount of enzyme or none and thus limited activation of prodrug.

The c-erbB-2 promoter has been sequenced to −1500 and may be obtained by reference to Hudson et al, (1990) J. Biol. Chem. 265; 4389–4393. The major start site of transcription has been determined by Ishii et al (1987) Proc. Natl. Acad. Sci. 84; 4374–4378 and Tal et al (1987) Mol. Cell Biol. 7; 2597–2601. This start site is referred to as +1 and this numbering is referred to herein. Translation of c-erbB-2 starts at +178. The promoter has a CAAT box at −75 and a TATA box at −25.

Hollywood and Hurst (1993) EMBO J. 12; 2369–2375 report that in mammary cells, regions of the promoter at −100 and −213 are important for the regulation of transcription. (see also Sarkar et al (1994) J. Biol. Chem. 269; 12285–12289).

In order to achieve expression from a vector utilizing the c-erbB-2 promoter, it is desirable to use the c-erbB-2 promoter region from the CAAT box, and preferably the TATA box, upstream to include sequence elements responsible for specificity of expression in particular tissues, such as those found for mammary cells by Hollywood and Hurst (ibid). The promoter will thus desirably include at least all the nucleotides upstream (5') of the CAAT box to about the 250th, eg. 300th, 400th, 500th, 600th, 700th, 800th, 900th or further nucleotide 5' to the start of transcription. It is also preferred to include the TATA box. Optionally, the c-erbB-2 sequences downstream of the TATA box to the start of translation at +178 may also be used.

Although the human c-erbB-2 promoter sequence is preferred, modified promoter sequences which are capable of selectively hybridizing to the human sequence may also be used. A promoter sequence capable of selectively hybridizing to the human promoter sequence will be generally at least 70%, preferably at least 80 or 90% and more preferably at least 95% homologous to the promoter region or fragment thereof over a region of at least 20, preferably at least 30, for instance 40, 60 or 100 or more contiguous nucleotides.

In general, those of skill in the art will appreciate that some regions of the promoter such as those at −213 will need to be retained to ensure tumour specificity of expression from the vector whereas other regions of the promoter may be modified or deleted without significant loss of specificity. Thus, modified promoters which are transcriptionally regulated substantially to the same degree as human c-erbB-2 are preferred. The degree of regulation of such candidate promoters can be tested and assessed by those of skill in the art using for example CAT assays in accordance with those described by Hollywood and Hurst (ibid).

"Operably linked" refers to a juxtaposition wherein the promoter and the enzyme-coding sequence are in a relationship permitting the coding sequence to be expressed under the control of the promoter. Thus, there may be elements such as 5' non-coding sequence between the promoter and coding sequence which is not native to either the promoter nor the coding sequence. Such sequences can be included in the vector if they do not impair the correct control of the coding sequence by the promoter.

Other suitable promoters include viral promoters such as mammalian retrovirus or DNA virus promoters. Suitable promoters include those used in vectors described above, e.g. MLV, CMV, RSV and adenovirus promoters. Preferred adenovirus promoters are the adenovirus early gene promoters. Strong mammalian promoters may also be suitable. An example of such a promoter is the EF-1α promoter which may be obtained by reference to Mizushima and Nagata ((1990), Nucl. Acids Res. 18; 5322). Variants of such promoters retaining substantially similar transcriptional activities may also be used.

The invention provides a viral vector comprising a c-erbB-2 promoter operably linked to a gene encoding a carboxypeptidase enzyme, the enzyme being capable of converting a prodrug into an active drug. The invention also provides a kit which comprises a vector as defined above together with a prodrug which is capable of being converted to an active drug by the enzyme encoded by the vector. In another aspect, the invention provides a vector as defined above or a kit as defined above for use in a method of treatment of the human or animal body, and in particular a method of treatment of tumours in which the c-erbB-2 proto-oncogene is overexpressed. In a further aspect, the invention provides a method of treatment of tumours, and in particular a method of treatment of tumours in which the c-erbB-2 proto-oncogene is overexpressed, which method comprises administering to an individual with a tumour (i) an effective amount of a vector as defined above, and (ii) an effective amount of a prodrug capable of being converted to an active drug by the enzyme encoded by the vector.

D. Prodrugs

The prodrug for use in the system will be selected to be compatible with the enzyme, ie. such that the enzyme will be capable of converting the prodrug into an active drug. Desirably, the toxicity of the prodrug to the patient being treated will be at least one order of magnitude less toxic to the patient than the active drug. Preferably, the active drug will be several, eg 2, 3, 4 or more orders of magnitude more toxic. Suitable prodrugs include nitrogen mustard prodrugs and other compounds such as those described in W088/07378, W089/10140, W090/02729, W091/03460, EP-A-540 263, W094/02450, W095/02420 or W095/03830 which are incorporated herein by reference.

E(i)—Nitrogen mustard prodrugs

Nitrogen mustard prodrugs include compounds of the formula:

where Ar represents an optionally substituted ring aromatic ring system, R—NH is the residue of an α-amino acid R—NH$_2$ or oligopeptide R—NH$_2$ and contains at least one carboxylic acid group, and M represents a nitrogen mustard group.

The residue of the amino acid R—NH is preferably the residue of glutamic acid. It is disclosed in W088/07378 that the enzyme carboxypeptidase G2 is capable of removing the glutamic acid moiety from compounds of the type shown above, and the removal of the glutamic acid moiety results in the production of an active nitrogen mustard drug.

Thus nitrogen mustard prodrugs of use in the invention include the prodrugs of generic formula I of W094/02450 and salts thereof, and in particular those of formula (I):

wherein $R^1$ and $R^2$ each independently represent chlorine, bromine, iodine, OSO$_2$Me, OSO$_2$phenyl (wherein phenyl is optionally substituted with 1,2,3,4 or 5 substituents independently selected from C$_{1-4}$ alkyl, halogen, —CN or NO$_2$);

$R^{1a}$ and $R^{2a}$ each independently represents hydrogen, C$_{1-4}$ alkyl or C$_{1-4}$ haloalkyl;

$R^3$ and $R^4$ each independently represents hydrogen, C$_{1-4}$ alkyl or C$_{1-4}$ haloalkyl;

n is an integer from 0 to 4;

each $R^5$ independently represents hydrogen, C$_{1-4}$ alkyl optionally containing one double bond or one triple bond, C$_{1-4}$ alkoxy, halogen, cyano, —NH$_2$, —CONR$^7$R$^8$ (wherein R$^7$ and R$^8$ are independently hydrogen, C$_{1-6}$ alkyl or C$_{3-6}$ cycloalkyl) or two adjacent $R^5$ groups together represent a) C4 alkylene optionally having one double bond;

b) C3 alkylene; or c) —CH=CH—CH=CH—, —CH=CH—CH2— or —CH2—CH=CH— each optionally substituted with 1, 2, 3 or 4 substituents said substituents each independently selected from the group consisting of C$_{1-4}$ alkyl, C$_{1-4}$ alkoxy, halogen, cyano and nitro;

X is a group —C(O)—, —O—C(O)—, —NH—C(O)— or —CH$_2$—C(O)—; and

Z is a group —CH$_2$—T—C(O)—OR$^6$ where T is CH$_2$, —O—, —S—, —(SO)— or —(SO$_2$)—, and R$^6$ is hydrogen, C$_{1-6}$ alkyl, C$_{3-6}$ cycloalkyl amino, mono- di-C$_{1-6}$ alkylamino or mono or diC$_{3-6}$ cycloalkyl amino, provided that when R$^6$ is hydrogen T is —CH$_2$—; and physiologically acceptable derivatives, including salts, of the compounds of formula (I).

Halogen includes fluorine, chlorine, bromine and iodine. Preferred values for the groups $R^{1a}$ and $R^{2a}$ are methyl and hydrogen, especially hydrogen. Preferred values for the groups $R^3$ and $R^4$ are hydrogen, methyl and trifluoromethyl, especially hydrogen. Preferred values for the groups $R^1$ and $R^2$ are I, Br, Cl, OSO$_2$Me and OSO$_2$phenyl wherein phenyl is substituted with one or two substituents in the 2 and/or 4 positions. I, Cl and OSO$_2$Me are especially preferred.

Preferred values for $R^5$ when n is an integer from 1 to 4 are fluorine, chlorine, methyl-CONH$_2$ and cyano. Preferably, n is 0, 1 or 2. When n is 1 or 2 it is preferred that $R^5$ is fluorine at the 3 and/or 5 positions of the ring. The group X is preferably —C(O)—, —O—C(O)— or —NH—C(O)—. Z is preferably a group —CH$_2$CH$_2$—COOH.

Preferred specific compounds include:

N-4-[(2-chloroethyl)(2-mesyloxyethyl)amino]benzoyl-L-glutamic acid (referred to below as "CMDA") and salts thereof;

N-(4-[bis(2-chloroethyl)amino]-3-fluorophenylcarbamoyl)-L-glutamic acid and salts thereof;

N-(4-[bis(2-chloroethyl)amino]phenylcarbamoyl)-L-glutamic acid and salts thereof;

N-(4-[bis(2-chloroethyl)amino]phenoxycarbonyl)-L-glutamic acid and salts thereof; and N-(4-[bis(2-iodoethyl)amino]phenoxycarbonyl)-L-glutamic acid and salts thereof.

Particular sub-groups of the compounds of the present invention of interest may be obtained by taking any one of the above mentioned particular or generic definitions for $R^1$-$R^4$, $R^5$, X or W either singly or in combination with any other particular or generic definition for $R^1$-$R^4$, $R^5$, X or W.

Prodrugs which are more lipophilic than compounds of the prior art such as those disclosed in W088/07378 are of use in the system of the invention, including compounds of the formula (II):

(II)

wherein $R^1$, $R^2$, $R^5$, n and Z are as defined for compounds of the formula (I) above;

m is an integer from 0 to 4, $Z^1$ and $Z^2$ are each independently —O— or —NH—; and $R^9$ is hydrogen, t-butyl or allyl;

and physiologically acceptable derivatives of the compound of formula (I). Preferred values of $R^1$, $R^2$, $R^5$, n and Z are as defined above for compounds of the formula (I). Preferred values of m are 0, 1 or 2 as defined for n above. $R^9$ is preferably hydrogen, but can be protected especially during synthesis by groups such as allyl or t-butyl.

These prodrugs can be activated at the site of a tumour by a carboxypeptidase enzyme, for example, CPG2 as disclosed in WO88/07378 or WO94/02450.

Compounds of the formula (II) may be made using reactions and methods known per se in the art of chemistry. The following methods are of particular use:

A: Compounds of formula (II) where $Z^1$ is —O—

Compounds of the formula (I) in which $Z^1$ is —O— may be made by reacting a nitrogen mustard of formula (III)

(III)

where $R^1$, $R^2$, and $R^5$ and n are as defined above and $Z^4$ is —O— with a linker of formula (IV)

(IV)

where $R^5$, m, $Z_2$, $R^9$ and $Z^3$ are as defined above, and Q is hydrogen or a leaving group. This reaction may be done in aprotic solvents in the presence of a base, for example DMF and triethylamine.

Preferred leaving groups Q include a succinimidyl group, a 4-nitrophenyl carbonate group, a pentafluorophenyl carbonate and a tetrachloroethyl group $CH(Cl)CCl_3$.

(ii) Compounds of the formula (III) may be made starting from 4-nitrophenol optionally substituted with the group(s) $R^5_{(n)}$ (as defined above). The phenolic group is protected as an adamantanyloxycarbonyl-derivative (by reacting the starting materials with adamantanyl-fluoroformate and triethylamine in THF at room temperature). The protected 4-nitrophenyl carbonate is reduced to the corresponding amine by hydrogen transfer in ethanol using ammonium formate and Pd/C 10% as catalyst at rt. The amine is then hydroxyethylated with ethylene oxide in AcOH at 20° C. and then reacted to the desired nitrogen mustard. Reference may be made to EP-A-433 360 or EP-A-490970 for suitable conditions. The compounds may be purified by column chromatography. Deprotection to remove the adamantyl group may be carried out in trifluoroacetic acid.

(iii) Alternatively, the nitrogen mustard of formula (III) may be activated as a chloroformate by treatment with phosgene or triphosgene in an aprotic solvent and triethylamine followed by coupling with a compound of formula (V):

(V)

where $R^5$, m, $Z^2$, $R^9$ and $Z^1$ are as defined above. This may be carried out in THF or other aprotic solvents in the present of a base (for example triethylamine or pyridine).

(iv) A further alternative route of synthesis of compounds of the formula (II) in which $Z^1$ is —O— involves direct coupling of 4-nitrophenol optionally substituted with the group(s) $R^5_{(n)}$ (as defined above) with the compound of the formula (IV) or by reaction of the said optionally substituted 4-nitrophenol compound chloroformate with the compound of formula (IV), followed in each case by the reaction described above to convert the nitro group, via an amine, to a mustard group.

B: Compounds of formula (II) where $Z^1$ is —NH—

(i) Compounds of the formula (II) in which $Z^1$ is —NH— may be made by reaction of a compound of formula (III) in which $Z_4$ is —NH— with a linker of the formula (IV) in aprotic solvents and in the presence of a base. Compounds of the formula (III) in which $Z^4$ is —NH— may be made from a 1-halo-4-nitrobenzy compound, optionally substituted with the group(s) $R^5_{(n)}$ (as defined above). This is converted to the corresponding 1-bis-hydroxyethylamino-4-nitro-benzyl compound by reaction with diethanolamine with heat and the resulting product purified by column chromatography. The corresponding 4-nitro nitrogen mustard may be made by for example mesylation using mesyl chloride in pyridine and subsequent reaction to other halo mustards, e.g. bromo or iodo mustards if required. The 4-nitro group may be reduced by hydrogen transfer in ethanol using ammonium formate and a Pd/C 10% catalyst at 20° C.

(ii) Alternatively the 1-bis-hydroxyethylamino-4-nitrobenzyl compound mentioned above can be reduced using ammonium formate and Pd/C 10% as catalyst in ethanol at 20° C. to provide the corresponding phenylenediamino derivative. This derivative can be converted into the corresponding 4-amino nitrogen mustard as described in the above paragraph, e.g. initially by reaction with mesyl chloride.

C: Compounds of the formula (IV) in which $Z^2$ is —NH—

(i) Compounds of the formula (IV) in which $Z^2$ is —NH— may be made from a 4-nitro benzylic alcohol optionally substituted with the group(s) $R^5_{(n)}$ (as defined above). The hydroxyl function is protected as a pyranyl- or t-butyl-dimethylsilyl (TBDMSi) -ether by treatment at 20° C. with 3,4-2H-dihydropyran and pyridinium-p-toluensulfonate (PPTS) in an aprotic solvent or with TBDMSi chloride and imidazole in dimethylformamide (DMAC), respectively. The intermediate thus obtained is reduced to the corresponding amine by hydrogen transfer in ethanol using ammonium formate and Pd/C 10% as catalyst at 20° C. This amine is converted to a glutamyl ester intermediate of formula (VI):

(VI)

where $R^5$, m, $R^9$ and $Z^1$ are as defined above, $Z^2$ is —NH— and Pr is the pyranyl- or t-butyl-dimethylsilyl (TBDMSi)-ether protecting group. This may be done by treating the amine with triphosgene and triethylamine in toluene at 60° C. to provide the corresponding isocyante, which is treated with a glutamate derivative of formula $R^9$—C(O)—CH(NH$_2$)—$Z^1$ where $R^9$ and Z are as defined above. Alternatively the corresponding glutamyl-isocyanate obtained from the corresponding glutamate by treatment with triphosgene and triethylamine in toluene at −78° C. may be reacted with the amine in a one pot procedure.

(ii) The compound of formula (VI) is deprotected to remove the TBDMSi or pyranyl groups by treatment with mild acidic media (AcOH, THF and H20 or PPTS, EtOH, 55° C.). This yields a compound of formula (VI) in which Pr is hydrogen. Compounds of the formula (IV) in which Q is a leaving group may be prepared using standard reactions known in the art.

(iii) For example where Q is a succinimidyl group the compound of formula (VI) where Pr is hydrogen may be treated with disuccinimidyl-carbonate and triethylamine in acetonitrile. Where a 4-nitrophenyl carbonate group is desired treatment with 4-nitrophenyl chlorformate and triethylamine in THF may be used. A pentafluorophenyl carbonate may be added by in situ phosgenation of pentafluorophenol followed by coupling to the linker of formula (VI) in which Pr is hydrogen.

D: Compounds of the formula (IV) in which $Z^2$ is —O—

(i) The starting materials for the linkers possessing a carbamic bond are unsubstituted or substituted (with the group(s) $R^5_{(n)}$ (as defined above)) 4-hydroxy-benzylic alcohols. These type of linkers may require an extra electron withdrawing group on the aromatic nucleus in order to undergo 1,4-elimination. The 4-hydroxy group is specifically protected as an acetate by treating the starting material with acetyl-v-triazolo-[4,5-b]pyridine, 1N NaOH in THF at 20° C. The alcohol function of the acetate is further protected as pyranyl- or TBDMSi-ether by the procedures described in section C above. The acetate function is then deprotected to restore the 4-hydroxy group in NaHCO3 aq. MeOH at 20° C. The resulting phenol compounds are reacted in a one pot procedure with a protected glutamyl-isocyanate as described in section C(i) above. This yields a compound of the formula of (VII) as shown above in which $Z^2$ is —O— and Pr is the pyranyl- or t-butyl-dimethylsilyl (TBDMSi)-ether protecting group.

(ii) Deprotection of this compound yields a compound of the formula (VI) in which Pr is hydrogen. This may be converted to compounds of the formula (IV) by methods analogous to those described in sections C(ii) and (iii) above.

E: Alternative synthesis of compounds of formula (III)

Compounds of the formula (III) in which Q is hydrogen, fluoro, chloro, bromo or —O—(N-succinimide) may also be obtained by reference to WO95/02420 or WO95/03830.

E(ii). Other prodrugs

Further prodrugs suitable for use in the invention include those of the general formula: FTLi-(PRT)$_m$, or salts thereof where FTLi is a ras inhibitor such as a farnesyltransferase inhibitor compound and PRT represents m' protecting groups capable of being cleaved from the ras inhibitor by the action of an enzyme, where m' is an integer from 1 to 5. Such compounds are disclosed in WO95/03830.

Suitable FLTi's include those of the formula

-continued where $R_{3a}$ and $R_{4a}$ are the side chains of naturally occurring amino acids (for example —$CH_3$, —$CH(CH_3)_2$, —$CH_2CH(CH_3)_2$, —$CH(CH_3)CH_2CH_3$, —$CH_2OH$, —$CH_2CH_2SCH_3$, —$CH(OH)CH_3$), including their oxidized forms (for example, methionine sulfoxide or methionine sulfone), or are substituted or unsubstituted aliphatic, aromatic or heteroaromatic groups, preferably cyclohexyl, phenyl, pyridyl, imidazolyl or saturated or unsaturated branched or straight chains of 2 to 8 carbon atoms optionally substituted with an aromatic or heteroaromatic ring;

$X_{1a}$ is $CH_2CH_2$, trans $CH=CH$ or $CH_2NH$; and $X_{2a}$ is $(CH_2)_n$ wherein n is 0, 1 or 2. Preferably $R_{3a}$ and $R_{4a}$ both represent $CH(CH_3)CH_2CH_3$.

Suitable FLTi compounds including those of the above formulae may be obtained by reference to WO95/03830.

A further group of prodrugs are tyrphostin compounds of the general formula: PTKi-PRT$_{m'}$, where PTKi is a compound with PTK (protein tyrosine kinase) inhibitory activity, PRT is a protecting group capable of being cleaved from the PTK inhibitor by the action of an enzyme and m' is an integer from 1 to 5.

Suitable PTKs include tyrphostins. Tyrphostins are low molecular weight (e.g. less than 2,000) styryl containing inhibitors of protein tyrosine kinase which are capable of binding to the subsite of protein tyrosine kinase domains. Suitable tyrphostins include those described by Gazit et al (Gazit et al, J. Med. Chem. (1989) 32, 2344) and Gazit et al (J. Med. Chem. (1991) 43; 1896–1907) and especially tyrphostins of the general formula:

where $X^1$ represents carbon, a nitrogen or a group N→O; n is an integer from 1 to 3; each group $R^{10}$, which may be the same or different is hydrogen, hydroxy, mercapto, carboxy, formyl, $C_{1-4}$alkyl, $C_{2-4}$ alkenyl, $C_{1-4}$alkoxy, $C_{1-4}$alkylthio, carboxy$C_{1-4}$alkyl, carboxy$C_{2-4}$ alkenyl, $C_{1-4}$alkylsulphoxy, halo (ie. fluoro, chloro, bromo or iodo), nitro, amino, $C_{1-4}$alkylamino, or $C_{1-4}$dialkylamino, or when n is 2 or 3 two $R^{10}$ groups may together form a methylenedioxy or ethylenedioxy group; $R^{11}$ is hydrogen, hydroxy, $C_{1-4}$alkyl or together with position 2 of the ring to which the group(s) $R^{10}$ is(are) attached forms a 5 or 6 membered aliphatic or heterocyclic ring, said 5 or 6 membered ring optionally containing a ketone group; and $R^{12}$ is cyano, carboxy, carbamoyl, thiocarbamoyl, a group $C(O)HNCH_2CN$, a group $C(NH_2)=C(CN)_2$, an alpha keto group $C(O)R^{13}$ where $R^{13}$ is 3,4-dihydroxyphenyl or 2-thiophenyl or an alpha amido group $C(O)NHR^{14}$ where $R^{14}$ is benzyl, phenyl or 2,4-dimethoxyphenyl; provided that at least one of the groups $R^{10}$ and $R^{11}$ is mercapto, hydroxy or amino.

In a preferred embodiment, $X^1$ is C; n is an integer from 1 to 3; each group $R^{10}$, which may be the same or different is hydrogen, hydroxy, carboxy, formyl, $C_{1-4}$alkyl, $C_{2-4}$ alkenyl, $C_{1-4}$alkoxy, carboxy$C_{1-4}$alkyl, carboxy$C_{2-4}$ alkenyl, halo (ie. fluoro, chloro, bromo or iodo), nitro, amino, $C_{1-4}$ alkylamino, or $C_{1-4}$dialkylamino, or when n is 2 or 3 two $R^{10}$ groups may together form a methylenedioxy or ethylenedioxy group; $R^{11}$ is hydrogen, hydroxy or $C_{1-4}$alkyl; and $R^{12}$ is cyano, carboxy, carbamoyl, thiocarbamoyl, a group $C(O)HNCH_2CN$ or a group $C(NH_2)=C(CN)_2$. Most preferably, $X^{10}$ represents carbon, n is an integer from 1 to 3; each group $R^{10}$, which may be the same or different is hydrogen, hydroxy or amino; $R^{11}$ is hydrogen or hydroxy; and $R^{12}$ is cyano, a group $C(O)HNCH_2CN$, a group $C(NH_2)=C(CN)_2$, an alpha keto group $C(O)R^{13}$ where $R^{13}$ is 3,4-dihydroxyphenyl, or an alpha amido group $C(O)NHR^{14}$ where $R^{14}$ is benzyl; provided that at least one of the groups $R^{10}$, $R^{11,}$ and $R^{12}$ are hydroxy or amino. Preferably, $R^{10}$ is hydroxy or amino. When $R^{11}$ forms a 5 or 6 membered ring with $R^{10}$ preferred rings include heterocyclic rings wherein the ring contain one nitrogen atom and 4 or 5 carbon atoms. The total number of atoms includes the 2 carbon atoms of the ring to which the group(s) $R^{10}$ is(are) attached.

Suitable tyrphostins such as the above may be obtained by the methods disclosed in, or analogous to those of, WO95/02420, Gazit et al 1989 and 1991, ibid, which are incorporated herein by reference.

Tyrphostins may be linked to any suitable protecting group which is removable by an enzyme. Suitable protecting groups PRT may be found by reference to WO95/03830 or WO95/02420 and may be of the structure:

where $Z^1$ is as defined above or S, m' is an integer from 1 to 5, Ph is a phenylene ring optionally substituted by from 1 to 4 groups $R^5$ (which may be the same or different) as defined above and glu is a group —CHZ—C(O)—$OR^9$ where Z and $R^9$ are as defined above.

E(iii). Derivatives

Physiologically acceptable derivatives of said prodrug include salts, amides, esters and salts of esters. Esters include carboxylic acid esters in which the non-carbonyl moiety of the ester grouping is selected from straight or branched chain $C_{1-6}$alkyl, (methyl, n-propyl,, n-butyl or t-butyl); or $C_{3-o}$cyclic alkyl (e.g. cyclohexyl). Salts include physiologically acceptable base salts, eg derived from an appropriate base, such as alkali metal (e.g. sodium), alkaline earth metal (e.g. magnesium) salts, ammonium and $NR_{4}"$ (wherein R" is $C_{1-4}$ alkyl) salts. Other salts include acid addition salts, including the hydrochloride and acetate salts. Amides include non-substituted and mono- and di-substituted derivatives.

F. Applications of the invention

The system of the invention can be used in a method of treatment of the human or animal body. Such treatment includes a method of treating the growth of neoplastic cells which comprises administering to a patient in need of treatment the system of the invention. It is also possible that the invention may be used to treat cells which are diseased through infection of the human or animal body by bacteria, viruses or parasites. Viral late promoters often rely on viral proteins that are made early in the infection. The viral coat proteins which are expressed on the surface of an infected cell may be used as a target for getting the gene into the cell. If a viral late promoter is then used to direct expression of the GDEPT enzyme, any infected cells will express the protein, and specifically, cells which have been infected, for some time. This may be sufficient to kill the infected cells. For parasites, a parasitic promoter and parasite surface proteins, may be used to direct expression and infect the parasites respectively.

For a bacteria, all the delivery systems will probably need to be changed to use bacterial viruses, although a specific promoter should be easier to define.

For use of the vectors in therapy, the vectors will usually be packaged into viral particles and the particles delivered to the site of the tumour, as described in for example Ram et al (ibid). The viral particles may be modified to include an antibody, fragment thereof (including a single chain) or tumour-directed ligand to enhance targetry of the tumour. Alternatively the vectors may be packaged into liposomes. The liposomes may be targeted to a particular tumour. This can be achieved by attaching a tumour-directed antibody to the liposome. Viral particles may also be incorporated into liposomes. The particles may be delivered to the tumour by any suitable means at the disposal of the physician. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a prodrug will be acceptably low, given the nature of the disease being treated. Ultimately, this will be determined by the physician.

Suitable liposomes include, for example, those comprising the positively charged lipid (N[1-(2,3-dioleyloxy) propyl]-N,N,N-triethylammonium (DOTMA), those comprising dioleoylphosphatidyl-ethanolamine (DOPE), and those comprising 3β[N-(n',N'-dimethyl-aminoethane)-carbamoyl]cholesterol (DC-Chol).

One suitable route of administration is by injection of the particles in a sterile solution. While it is possible for the prodrugs to be administered alone it is preferable to present them as pharmaceutical formulations. The formulations comprise a prodrug, together with one or more acceptable carriers thereof and optionally other therapeutic ingredients. The carrier or carriers must be "acceptable" in the sense of being compatible with the other ingredients of the formulation and not deleterious to the recipients thereof, for example, liposomes. Suitable liposomes include, for example, those comprising the positively charged lipid (N[1-(2,3-dioleyloxy) propyl] -N,N,N-triethylammonium (DOTMA), those comprising dioleoylphosphatidylethanolamine (DOPE), and those comprising 3β[N-(n',N'-dimethylaminoethane)-carbamoyl]cholesterol (DC-Chol).

Viruses, for example isolated from packaging cell lines may also be administered by regional perfusion or direct intratumoral direction, or direct injection into a body cavity (intracaviterial administration), for example by intraperitoneum injection.

It is also known that muscle cells can take up naked DNA and thus sarcomas may be treated using a vector system of the invention in which naked DNA is directly injected into the sarcoma.

Formulations suitable for parenteral or intramuscular administration include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets of the kind previously described.

It should be understood that in addition to the ingredients particularly mentioned above the formulations may include other agents conventional in the art having regard to the type of formulation in question. Of the possible formulations, sterile pyrogen-free aqueous and non-aqueous solutions are preferred.

The doses may be administered sequentially, eg. at daily, weekly or monthly intervals, or in response to a specific need of the patient.

Preferred routes of administration are oral delivery and injection, typically parenteral or intramuscular injection or intratumoural injection.

In using the system of the present invention the prodrug will usually be administered following administration of the vector encoding an enzyme. Typically, the vector will be administered to the patient and then the uptake of the vector by transfected or infected (in the case of viral vectors) cells monitored, for example by recovery and analysis of a biopsy sample of targeted tissue.

The exact dosage regime will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of both the prodrug and modified virus and administration by the intravenous route is frequently found to be the most practical. For glioblastoma the route is often intratumoural. A typical dosage range of prodrug generally will be in the range of from about 1 to 150 mg per kg per patient per day, which may be administered in single or multiple doses. Preferably the dose range will be in the range from about 10 to 75, e.g. from about 10 to 40, mg per kg per patient per day. Other doses may be used according to the condition of the patient and other factors at the discretion of the physician.

Tumours which may be treated using the system of the present invention include any tumours capable or being treated by a GDEPT or VDEPT system and thus are not limited to any one particular class of tumours. Particularly suitable tumour types include breast, colorectal and ovarian tumours, as well as pancreatic, melanoma, glioblastoma, hepatoma, small cell lung, non-small cell lung, muscle and prostate tumours.

The system of the invention may also be used to treat infectious diseases, for example, and any other condition which requires eradication of a population of cells.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptons of the disease.

The following Examples illustrate the invention.

PREPARATIVE EXAMPLE 1

The native CPG2 protein contains a signal peptide which serves to export it out of bacterial cells into the extracellular environment. In order to ensure that the signal peptide did not direct the export of CPG2 from mammalian cells, PCR directed site specific mutagenesis was used to delete the signal peptide from the CPG2 gene. This was achieved using the PCR primer #4476: 5'>CGC GGA TCC GCC CTG GCC CAG AAG CGC<3' (SEQ ID NO:2) in conjunction with primer #4477: 5'>CGC GAA TTC CTT GCC GGC GCC CAG ATC<3' (SEQ ID NO:3)

Primer #4476 was used to alter codons 21 and 22 of the CPG2 gene into a Bamh1 restriction endonuclease site. Primer #4477 was used to change codon 416 (the natural stop codon of CPG2) into an EcoR1 restriction endonuclease site. A PCR generated fragment, containing the entire CPG2 open reading frame was generated and digested with BamH1 and EcoR1 and cloned into those sites of the plasmid MLVβplink (Dalton and Treisman (1992), Cell 68, 597–612). This results in a CPG2 protein which has the structure (SEQ ID NO:4): Met-Ala-Gly-Ser-(CPG2 codons 23 to 415)-Glu-Phe-Leu-Glu-Ile-Asp, and therefore lacks the signal peptide. The plasmid is refered to as "MLVCPG2*" and the protein produced from it as CPG2*.

NIH3T3 cells were transfected with MLVCPG2*, or with MLVβplink as a control in order to determine whether CPG2 could be produced in mammalian cells. Transfection was performed using the lipid reagent lipofectAMINE (GibcoBRL). For transfection, 1×10$^5$ cells were plated into 35 mm tissue culture dishes and incubated at 37° C. overnight. The following day, lipofectAMINE:DNA complexes were prepared by combining 0.4 μg of plasmid with 6 μl of lipofectAMINE reagent (Gibco/BRL) in a total of 32 μl of PBSA; the complexes were incubated at room temperature for 15 minutes. The cells were washed twice with 2 ml of serum free DMEM medium and placed in 0.8 ml of serum free DMEM. The lipofectAMINE:DNA complexes were diluted into 0.2 ml of serum free medium and added to the cells. The cells were incubated with the lipofectAMINE:DNA complexes for 6 hours at 37° C., washed twice with 2 ml of DMEM medium containing 10% foetal calf serum (FCS) and placed into 2.5 ml 10%FCS/DMEM. After a further incubation period of 42 hours, the cells were washed twice with 5 ml PBSA and extracted on the tissue culture dishes into 50 μl of buffer A (250 mM Tris.HCl, 10%v/v glycerol, 1%v/v Triton X-100, pH7.5). The extract was transferred to 1.5 ml tubes, centrifuged at 13,000 rpm in a micro-fuge and the supernatants collected; the protein concentration was determined with the Bio-Rad protein assay kit, with BSA as a standard.

For protein-immunoblot analysis, 10 μl of each extract was combined with 10 μl of SDS sample buffer and the proteins were separated on a 10% SDS-polyacrylamide gel (Laemmli U.K. (1970) Nature 227; 680–685). The proteins in the gel were transferred to nitrocellulose by electroelution and the cell extracts analysed by protein immuno-blotting (Gershoni J. M. and Palade G. E. (1983) Anal. Biochemistry 131;1–15), using a CPG2 specific rabbit polyclonal antibody which was raised to CPG2 expressed in Sf9 insect cells. The antibody was used at a dilution of 1:1000 and the immunocomplexes detected using the ECL immunoblotting kit, according to the manufacturers instructions (Amersham).

The extracts were also tested for CPG2 enzyme activity by measuring their ability to cleave the CMDA prodrug into active drug, which can be detected by measuring the change in optical density absorbance at 305 nm. For the assay, 5 μg of NIH3T3 protein extracted in buffer A was incubated in 1 ml assay buffer (20 mM Tris.HCl, 1 mM MgCl2, 60 μM ZnCl2, pH 7.4) containing 50 μM CMDA prodrug, at 37° C. for 15 min. After incubation, EDTA was added to a final concentration of 10 mM and the change in absorbance at 305 nm was monitored and compared to that of the starting solution. A reduction in absorbance indicates conversion of the prodrug into drug and therefore by inference demonstrates the presence of CPG2; the enzyme activity is expressed in arbitrary units, compared to extraction buffer controls.

Figure 1A:
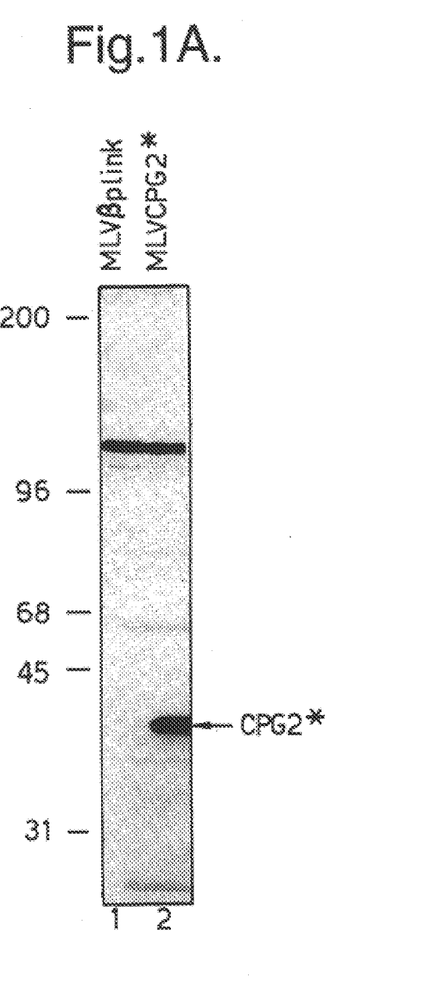
Figure 1B:
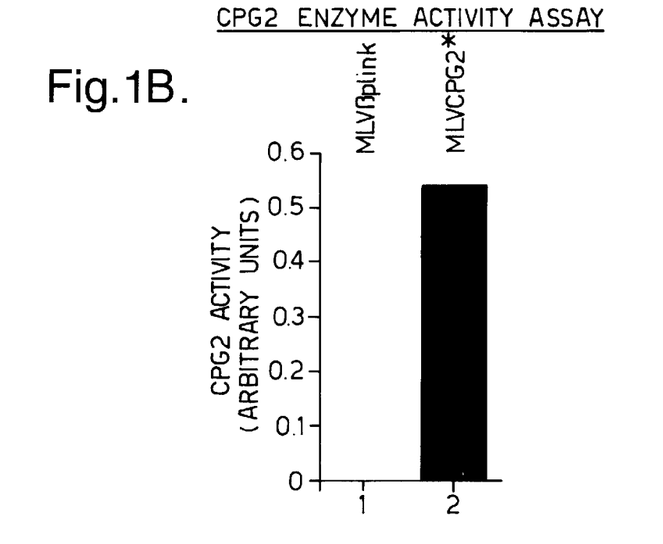

From the immunoblot analysis, it could be seen that extracts from cells transfected with MLVCPG2* contained a protein with an apparent Mr of ~40,000 which was recognised by the CPG2 antibody and which was not present in cells transfected with MLVβplink (FIG. 1A). When the enzymatic activity of these extracts was examined, CPG2 activity was detected in cell extracts from cells transfected with MLVCPG2* but not in extracts from cells transfected with MLVβplink (FIG. 1B). These data show that it is possible to express CPG2* inside mammalian cells in a form that is enzymatically active.

EXAMPLE 1

The internally expressed CPG2* was tested for its ability to direct cell death in NIH3T3 cells treated with prodrugs. Two sets of cells were prepared, each of which contained one dish of cells transfected with MLVβplink and one dish of cells transfected with MLVCPG2*. The cells were incubated for 42 hours following the transfection and then set 1 was incubated in the presence of prodrug vehicle (5 mM Hepes, 0.5%v/v DMSO, pH7.0; final concentrations) for 24 hours and set 2 were incubated with the CMDA prodrug (0.5 mM final concentration) for 24 hours. Following prodrug treatment, the cells were washed twice with 5 ml fresh medium and incubated for a further 24 hours. They were then passaged into fresh culture dishes, seeded at 1×10$^5$ cells/ 35 mm dish in 2 ml 10%FCS/ DMEM. After a further 72 hour incubation cell growth was assessed by thymidine incorporation. For thymidine incorporation, 1μCi of [methyl-$^3$H] thymidine was added to each well (2 ml medium) and incubated for 5 hours at 37° C. The cells were washed twice with PBSA (4° C.) and fixed with 5%w/v trichloro acetic acid (TCA) in water at 4° C. for 20 minutes. The TCA was removed and the cells washed twice with 2 ml methanol and air dried. The DNA was extracted with 1 ml 0.1M NaOH, 1%SDS at room temperature for 5 minutes, added to 4 ml scintillation fluid and the incorporated thymidine was determined by scintillation counting.

Figure 2:
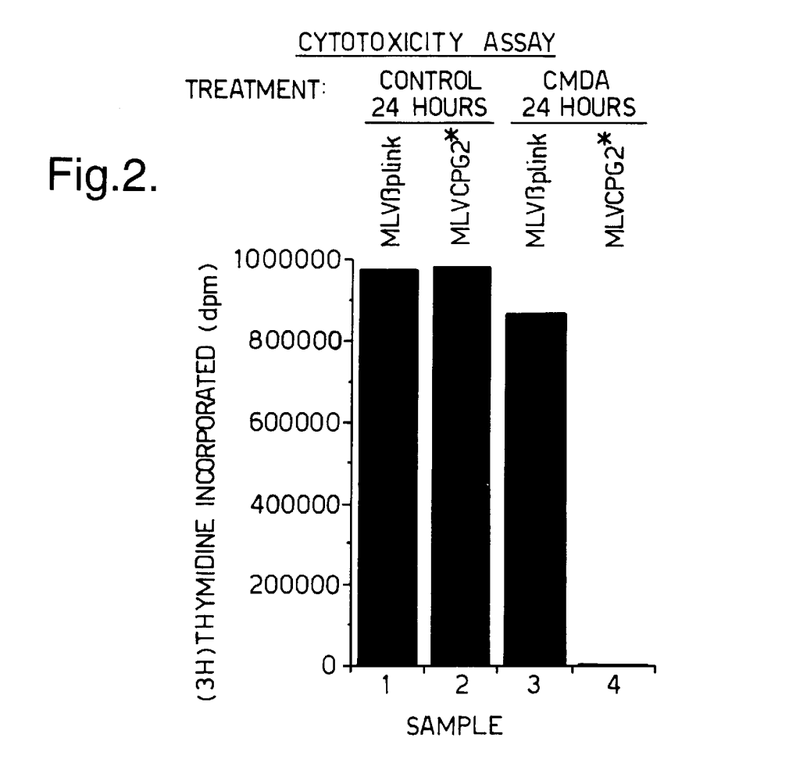
FIG. 2. Cytotoxicity assay NIH3T3 cells were transfected with MLVβplink (samples 1, 3) or MLVCPG2* (lanes 2, 4). Forty-two hours after transfection, the cells were treated with CMDA prodrug vehicle as a control (lanes 1, 2) or with CMDA prodrug for 24 hours (lanes 3, 4). After a recovery period, the cells were passaged into fresh tissue culture dishes and after three days, the viability of the cells determined by measuring [methyl-$^3$H]thymidine incorporation. The amount of incorporated thymidine is shown in terms of dpm for each sample.

Cells transfected with MLVCPG2* grew at the same rate as cells transfected with MLVβplink, indicating that expression of CPG2* in cells did not affect the growth of these cells (FIG. 2, compare samples 1,2). Treatment of the control cells with CMDA had only a minimal effect on their growth rate (FIG. 2, compare samples 1,3). By contrast, treatment of the cells expressing CPG2* with CMDA resulted in completed inhibition of thymidine incorporation and cell death (FIG. 2, compare samples 2,4). Thus, these data show that the enzyme CPG2 can be expressed in NIH3T3 cells in an active form which does not appear to affect the rate of growth of these cells. If cells expressing CPG2* are treated with 0.5M CMDA for 24 hours, 100% of the cells are killed.

PREPARATIVE EXAMPLE 2

1. Construction of the vector

An expression cassette was constructed by fusing the 1.2 kb HindIII/EcoR1 fragment from the plasmid pEF-Bos (Mizishuma and Nasgata (1990) NAR 18, 5322), which contains the EF1a promoter, first exon, first intron and a portion of the second exon to the β-globin gene at position −4 relative to the start of transcription of the β-globin gene. The Nco-1/HindIII fragment from the plasmid MLVβ-Plink, containing the polylinker and the β-globin 3' untranslated region was fused to the Nco-1 site of the β-globin gene, which is located across the β-globin start of translation (position +50, relative to the start of transcription), to provide a polylinker and 3,' untranslated region for proper mRNA processing.

This entire cassette was to be cloned into the vector pMC1Neo PolyA (Stratagene). pMC1Neo PolyA was first modified to destroy the Nco1 site located in the Neo$^R$ gene and to remove the BamHi, HincII and SaI1 sites located at the 3' end of the Neo$^R$ gene. The EF1α expression cassette was cloned as an HindIII fragment (end repaired) into the Xho1 (end repaired) site in the modified pMC1Neo PolyA plasmid. A vector with the EF1α promoter and the TK promoter (which drives expression of the Neo$^R$ gene) facing in opposite directions was chosen for the expression of CPG2*; the vector is referred to as pMCEF-Plink. CPG2* was cloned from pMLVCPG2* as an Nco1/Xba1 fragment into the Nco1/Xba1 sites of pMCEF-Plink; this plasmid is referred to as pMCEFCPG2*. As a control plasmid, the lacZ gene was also cloned into the Nco1/Xba1 sites pMCEF-Plink as a Nco1/Xba fragment from the plasmid MLVBlacZ; this is referred to as pMCEFlacZ.

2. Preparation of stable cell lines

Stable cell lines were prepared with NIH3T3 cells to constitutively express CPG2*, or as a control the lacZ gene product (β-galactosidase). In order to do this, NIH3T3 cells were transfected with pMCEF-CPG2* or pMCEFlacZ as described in Preparative Example 1, and two days after transfection, the cells were plated at low density into medium containing G418 at 1 mg/ml. Colonies coming from single cells could be observed about two weeks later and these were cloned and grown up individually. The expression of CPG2* was determined by immunoprotein blotting of 30μl of cell extract (extracted as described in Preparative Example 1) from each of the G418 resistant colonies with a CPG2 specific polyclonal antibody. The cell line #9 which expresses high levels of CPG2*. (FIG. 3A) and cell line #3, which expresses the β-galactosidase (see below) were selected for further investigation. The expression of CPG2* and β-galactosidase were verified in the cell lines, by enzymatic assay. For these assays, $1 \times 10^5$ cells for lines #3 and #9 were plated into 35 mm tissue culture dishes and incubated for 4 days.

Figure 3:
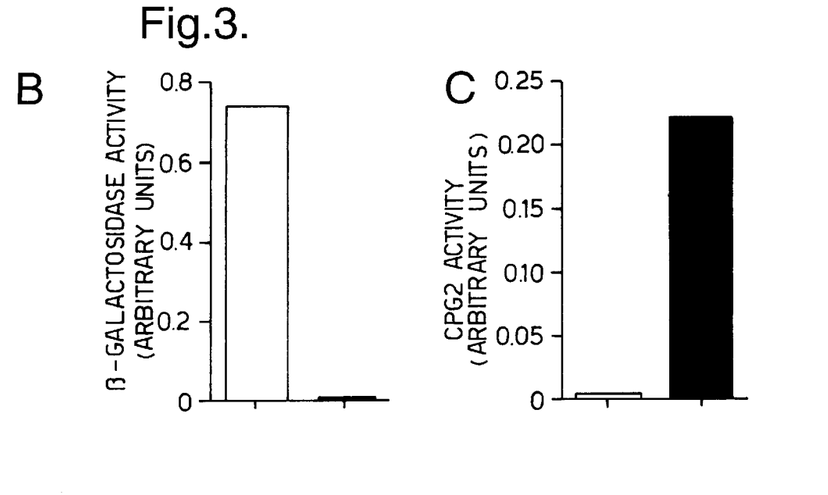
FIG. 3A shows the constitutive expression of CPG2* in NIH3T3 cells.
FIGS. 3B and 3C show in arbitrary units the enzymatic activity for β-galactosidase (A) and CPG2 (B) expressed in NIH3T3 cell lines #3 (open bar) and #9 (solid bar).
Figure 3A:
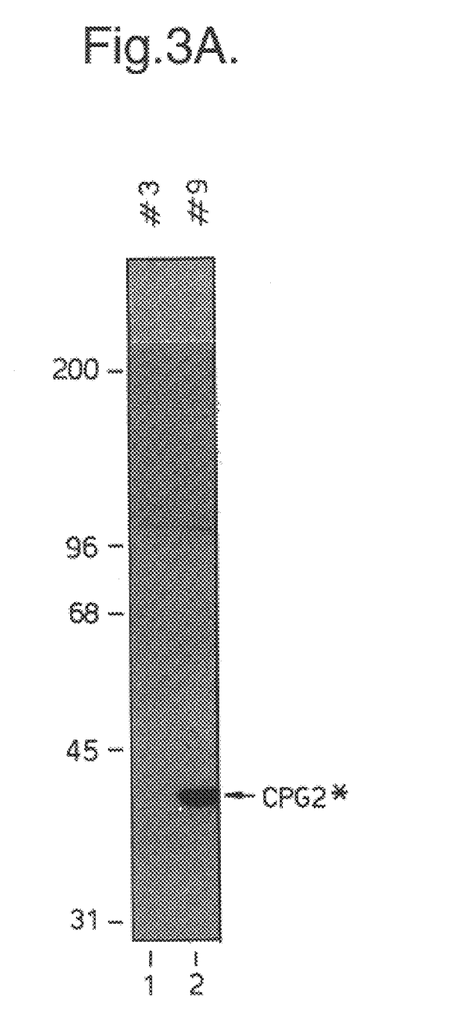

Cell extracts were prepared as described in Preparative Example 1 and 5 μg of protein was subjected to a CMDA degradation assay and a β-galactosidase assay (the CMDA assay is described in Preparative Example 1). For the assay of β-galactosidase activity in cells, 5 μg of extracted protein was added to 600 μl of assay buffer (40 mM $Na_2PO_4$, 26.7 mM $NaH_2PO_4$, 6.7 mMKCL, 1mMMgSO$_4$, 25 mM 2-mercaptoethanol, 50 mM Tris.HCL, 0.06%v/v Triton X-100, 2.2 mM o-nitrophenyl β-D-galactopyranoside) and incubated at 37° C. for 60 min. 250 μl of 1MNa$_2$CO$_3$ was added to the sample and the OD$_{420}$ was measured. The results in FIGS. 3B and 3C show that extracts from line #3 (open bars) contain high levels of β-galactosidase activity but no CPG2 activity. The extract from line #9 does not contain any detectable β-galactosidase activity but does contain detectable levels of CPG2 activity.

EXAMPLE 2

Figure 4:
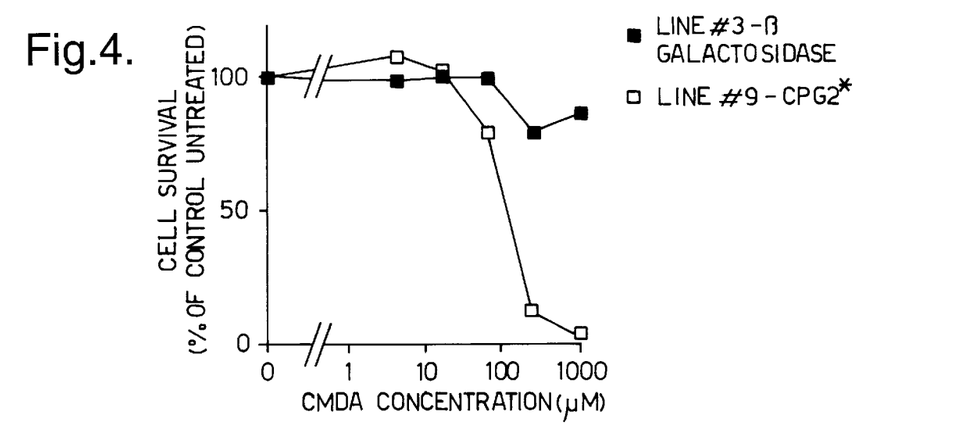
FIG. 4 shows cell survival versus CMDA concentration, as described in Example 2.

Cell lines #3 and #9 obtained in Preparative Example 2 were tested for cytotoxicity with the CMDA pro-drug. $1 \times 10^5$ cells were plated into each well of 24 well dishes, incubated for 40 hours and then treated with increasing concentrations of CMDA at 37° C. for 60 minutes. After a further 6 hour incubation, 10% of the cells were re-plated into 24 well dishes, incubated for a further 5 days and cell survival was determined by [$^3$H]-thymidine incorporation. The results in FIG. 4 show that cell line #3 (filled symbols) is not sensitive to even the highest concentration of CMDA tested, whereas #9 (open symbols) is sensitive in a dose dependent manner, showing an IC50 of ∼125 μM.

EXAMPLE 3

Figure 5:
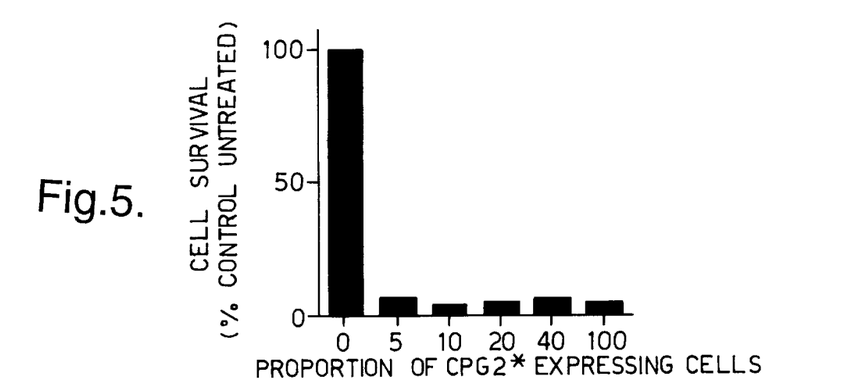
FIG. 5 shows cell survival versus proportion of CPG2* expressing cells, as described in Example 3.

The bystander effect was determined by mixing cell lines #3 and #9 obtained in Preparative Example 2 at a variety of concentrations as indicated and a total of $1 \times 10^5$ cells were plated per well in 24 well plates and incubated overnight. The cells were treated with 250 μM CMDA for 60 minutes as indicated and cell survival was determined as in Example 2. The results in FIG. 5 show that with these conditions, more than 95% of the cells are killed when only 5% of the total cell population express CPG2*: thus demonstrating that there is a substantial bystander effect with this system.

We claim:

1. A two component system which comprises: (a) vector comprising a promoter operably linked to a nucleic acid encoding a bacterial carboxypeptidase G2; and (b) a nitrogen mustard prodrug which is converted into an active drug by said carboxypeptidase, said nitrogen mustard prodrug being other than para-N-bis(2-chloroethyl) aminobenzoyl glutamic acid.

2. The system of claim 1 wherein said carboxypeptidase G2 is selected from the CPG2 of SEQ ID NO:1 or a CPG2 variant having truncations of amino acid sequence, or amino acid substitutions, deletions or insertions, wherein said variant retains the carboxypeptidase activity CPG2.

3. The system of claim 1 wherein said carboxypeptidase comprises an N-terminal or C-terminal truncation, wherein the truncated carboxypeptidase retains the carboxypeptidase activity CPG2.

4. The system of claim 2 wherein said CPG2 variant comprises an N-terminal or C-terminal truncation, wherein the truncated carboxypeptidase retains the carboxypeptidase activity CPG2.

5. The system of claim 1 wherein the promoter is tissue restricted.

6. The system of claim 5 wherein said promoter is a c-erbB2 promoter.

7. A method for testing the bystander effect of a prodrug comprising a nitrogen mustard compound which is converted into an active drug by the action of a bacterial carboxypeptidase G2, said method comprising:

providing NIH3T3 cells which have been transformed in vitrowith a vector comprising a promoter operably linked to a nucleic acid encoding a bacterial carboxypeptidase G2;

expressing said nucleic acid to produce said bacterial carboxypeptidase G2 in said cells;

mixing said cells expressing said bacterial carboxypeptidase G2 with a proportion of untransformed NIH3T3 cells to obtain a mixture of transformed and untransformed cells;

exposing said mixture to a prodrug which can be converted by said bacterial carboxypeptidase G2 into an active drug; and determining the bystander effect of said drug by measuring the number of dead cells in said mixture.

8. A method of treating isolated cells comprising transforming said cells in vitrowith a vector comprising a promoter operably linked to a nucleic acid encoding a bacterial carboxypeptidase G2 to produce transformed cells; expressing said nucleic acid sequence in said transformed cells to produce expressing cells; and treating said expressing cells with a nitrogen mustard prodrug which is converted by said bacterial carboxypeptidase G2 into an active drug, said drug being other than para-N-bis(2-chloroethyl) amino glutamic acid.

9. A method of killing isolated cells comprising transforming said cells in vitro with a vector comprising a promoter operably linked to a nucleic acid encoding a bacterial carboxypeptidase G2 to produce transformed cells; expressing said nucleic acid sequence in said cells to produce expressing cells; and treating said expressing cells with a nitrogen mustard prodrug which is converted by said bacterial carboxypeptidase G2 into an active drug such that said expressing cells are killed, said drug being other than para-N-bis(2-chloroethyl) amino glutamic acid.

10. A method of killing cells comprising transforming said cells in vitro with a vector comprising a promoter operably linked to a nucleic acid encoding a bacterial carboxypeptidase G2 to produce transformed cells; implanting said transformed cells into a host; expressing said DNA sequence within said implanted cells; treating said host with a nitrogen mustard prodrug which is converted to an active drug by said bacterial carboxypeptidase G2 such that said implanted cells are killed, said drug being other than para-N-bis(2-chloroethyl) amino glutamic acid.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 2048 base pairs
      (B) TYPE: nucleic acid
      (C) STRANDEDNESS: double
      (D) TOPOLOGY: circular    (ii) MOLECULE TYPE: DNA (genomic)

(xi) SEQUENCE DESCRIPTION: SEQ ID NO: 1:

```
ATCATGGATC CACGCACTGA AGGCGCGCGG CAAGACGCGC GGCGTGGCGA CGCTGTGCAT      60
```

-continued

```
CGGCGGGGGC GAAGGCACCG CAGTGGCACT CGAATTGCTA TAAGAACCAT GGCTGGGGAC      120

GCCCGACAAC AGGCGTCCAC CAGCTTTTTT CATTCCGACA ACCCGAACGA ACAATGCGTA      180

GAGCAGGAGA TTCC ATG CGC CCA TCC ATC CAC CGC ACA GCC ATC GCC GCC       230
            Met Arg Pro Ser Ile His Arg Thr Ala Ile Ala Ala
             1           5                  10

GTG CTG GCC ACC GCC TTC GTG GCG GGC ACC GCC CTG GCC CAG AAG CGC       278
Val Leu Ala Thr Ala Phe Val Ala Gly Thr Ala Leu Ala Gln Lys Arg
         15                  20                  25

GAC AAC GTG CTG TTC CAG GCA GCT ACC GAC GAG CAG CCG GCC GTG ATC       326
Asp Asn Val Leu Phe Gln Ala Ala Thr Asp Glu Gln Pro Ala Val Ile
         30                  35                  40

AAG ACG CTG GAG AAG CTG GTC AAC ATC GAG ACC GGC ACC GGT GAC GCC       374
Lys Thr Leu Glu Lys Leu Val Asn Ile Glu Thr Gly Thr Gly Asp Ala
 45              50                  55                  60

GAG GGC ATC GCC GCT GCG GGC AAC TTC CTC GAG GCC GAG CTC AAG AAC       422
Glu Gly Ile Ala Ala Ala Gly Asn Phe Leu Glu Ala Glu Leu Lys Asn
                 65                  70                  75

CTC GGC TTC ACG GTC ACG CGA AGC AAG TCG GCC GGC CTG GTG GTG GGC       470
Leu Gly Phe Thr Val Thr Arg Ser Lys Ser Ala Gly Leu Val Val Gly
             80                  85                  90

GAC AAC ATC GTG GGC AAG ATC AAG GGC CGC GGC GGC AAG AAC CTG CTG       518
Asp Asn Ile Val Gly Lys Ile Lys Gly Arg Gly Gly Lys Asn Leu Leu
         95                  100                 105

CTG ATG TCG CAC ATG GAC ACC GTC TAC CTC AAG GGC ATT CTC GCG AAG       566
Leu Met Ser His Met Asp Thr Val Tyr Leu Lys Gly Ile Leu Ala Lys
     110                 115                 120

GCC CCG TTC CGC GTC GAA GGC GAC AAG GCC TAC GGC CCG GGC ATC GCC       614
Ala Pro Phe Arg Val Glu Gly Asp Lys Ala Tyr Gly Pro Gly Ile Ala
125              130                 135                 140

GAC GAC AAG GGC GGC AAC GCG GTC ATC CTG CAC ACG CTC AAG CTG CTG       662
Asp Asp Lys Gly Gly Asn Ala Val Ile Leu His Thr Leu Lys Leu Leu
                 145                 150                 155

AAG GAA TAC GGC GTG CGC GAC TAC GGC ACC ATC ACC GTG CTG TTC AAC       710
Lys Glu Tyr Gly Val Arg Asp Tyr Gly Thr Ile Thr Val Leu Phe Asn
             160                 165                 170

ACC GAC GAG GAA AAG GGT TCC TTC GGC TCG CGC GAC CTG ATC CAG GAA       758
Thr Asp Glu Glu Lys Gly Ser Phe Gly Ser Arg Asp Leu Ile Gln Glu
         175                 180                 185

GAA GCC AAG CTG GCC GAC TAC GTG CTC TCC TTC GAG CCC ACC AGC GCA       806
Glu Ala Lys Leu Ala Asp Tyr Val Leu Ser Phe Glu Pro Thr Ser Ala
     190                 195                 200

GGC GAC GAA AAA CTC TCG CTG GGC ACC TCG GGC ATC GCC TAC GTG CAG       854
Gly Asp Glu Lys Leu Ser Leu Gly Thr Ser Gly Ile Ala Tyr Val Gln
205              210                 215                 220

GTC AAC ATC ACC GGC AAG GCC TCG CAT GCC GGC GCC GCG CCC GAG CTG       902
Val Asn Ile Thr Gly Lys Ala Ser His Ala Gly Ala Ala Pro Glu Leu
                 225                 230                 235

GGC GTG AAC GCG CTG GTC GAG GCT TCC GAC CTC GTG CTG CGC ACG ATG       950
Gly Val Asn Ala Leu Val Glu Ala Ser Asp Leu Val Leu Arg Thr Met
             240                 245                 250

AAC ATC GAC GAC AAG GCG AAG AAC CTG CGC TTC AAC TGG ACC ATC GCC       998
Asn Ile Asp Asp Lys Ala Lys Asn Leu Arg Phe Asn Trp Thr Ile Ala
         255                 260                 265

AAG GCC GGC AAC GTC TCG AAC ATC ATC CCC GCC AGC GCC ACG CTG AAC      1046
Lys Ala Gly Asn Val Ser Asn Ile Ile Pro Ala Ser Ala Thr Leu Asn
     270                 275                 280

GCC GAC GTG CGC TAC GCG CGC AAC GAG GAC TTC GAC GCC GCC ATG AAG      1094
Ala Asp Val Arg Tyr Ala Arg Asn Glu Asp Phe Asp Ala Ala Met Lys
285              290                 295                 300
```

```
ACG CTG GAA GAG CGC GCG CAG CAG AAG AAG CTG CCC GAG GCC GAC GTG       1142
Thr Leu Glu Glu Arg Ala Gln Gln Lys Lys Leu Pro Glu Ala Asp Val
                305                 310                 315

AAG GTG ATC GTC ACG CGC GGC CGC CCG GCC TTC AAT GCC GGC GAA GGC       1190
Lys Val Ile Val Thr Arg Gly Arg Pro Ala Phe Asn Ala Gly Glu Gly
                320                 325                 330

GGC AAG AAG CTG GTC GAC AAG GCG GTG GCC TAC TAC AAG GAA GCC GGC       1238
Gly Lys Lys Leu Val Asp Lys Ala Val Ala Tyr Tyr Lys Glu Ala Gly
                335                 340                 345

GGC ACG CTG GGC GTG GAA GAG CGC ACC GGC GGC GGC ACC GAC GCG GCC       1286
Gly Thr Leu Gly Val Glu Glu Arg Thr Gly Gly Gly Thr Asp Ala Ala
                350                 355                 360

TAC GCC GCG CTC TCA GGC AAG CCA GTG ATC GAG AGC CTG GGC CTG CCG       1334
Tyr Ala Ala Leu Ser Gly Lys Pro Val Ile Glu Ser Leu Gly Leu Pro
365                 370                 375                 380

GGC TTC GGC TAC CAC AGC GAC AAG GCC GAG TAC GTG GAC ATC AGC GCG       1382
Gly Phe Gly Tyr His Ser Asp Lys Ala Glu Tyr Val Asp Ile Ser Ala
                385                 390                 395

ATT CCG CGC CGC CTG TAC ATG GCT GCG CGC CTG ATC ATG GAT CTG GGC       1430
Ile Pro Arg Arg Leu Tyr Met Ala Ala Arg Leu Ile Met Asp Leu Gly
                400                 405                 410

GCC GGC AAG T GAATGCTGCC CCCCGGCTTT TCACTCGCGT TGCTCGTGTA             1480
Ala Gly Lys
        415

ACTCCACCCC CCGAGGGGGA GGCGCGGTCC GCCTTGGGGC GGCCCGGCGG CGACCGCCTC     1540

GTCACATAGA AGGAACTGCC ATGTTGTTGA CAGCAGACCA GGAAGCCATC CGCGACGCGG     1600

TGCGCGACTT CTCGCAAGCC GAACTCTGGC CCAACGCCGC GAATGGGGAC CGCGAGCACA     1660

GCTTTCCCAA GAGCCCACCA GGCCGTCGGC TGGCGTACGC AGTCTGCGTG CCCGAGGAGC     1720

ATGGCGGCGC CGGCCTCGAC TACCTCACCT CGCGCTGGTG CTGGAGGAGA TCGCGGCCGG     1780

CGACGGCGGA ACCAGCACCG CCATCAGCGT GACCAACTGC CCCGTCAACG CCATCCTCAT     1840

GCGCTACGGC AACGCGCAGC AGAAGAAGCA GTGGCTCGAG CCGCTGGCGC AGGGCCGGAT     1900

GCTCGGCGCC TTCTGCCTGA CCGAGCCGCA GGCCGGCAGC GATGCATCGA GCCTGCGCAC     1960

CACGGCGCGC AAGGACGGCG ACGGCTACGT GATCGACGGC GTGAAGCAGT TCATCACCAG     2020

CGGCAAGAAC GGCCAGGTGG CGGGATCC                                       2048

(2) INFORMATION FOR SEQ ID NO: 2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 2:

CGCGGATCCG CCCTGGCCCA GAAGCGC                                          27

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 3:

CGCGAATTCC TTGCCGGCGC CCAGATC                                          27
```

-continued (2) INFORMATION FOR SEQ ID NO: 4:

(i) SEQUENCE CHARACTERISTICS:
        (A) LENGTH: 403 amino acids
        (B) TYPE: amino acid
        (D) TOPOLOGY: linear     (xi) SEQUENCE DESCRIPTION: SEQ ID NO: 4:

```
Met Ala Gly Ser Ala Leu Ala Gln Lys Arg Asp Asn Val Leu Phe Gln
 1               5                  10                  15

Ala Ala Thr Asp Glu Gln Pro Ala Val Ile Lys Thr Leu Glu Lys Leu
            20                  25                  30

Val Asn Ile Glu Thr Gly Thr Gly Asp Ala Glu Gly Ile Ala Ala Ala
        35                  40                  45

Gly Asn Phe Leu Glu Ala Glu Leu Lys Asn Leu Gly Phe Thr Val Thr
50                  55                  60

Arg Ser Lys Ser Ala Gly Leu Val Val Gly Asp Asn Ile Val Gly Lys
65                  70                  75                  80

Ile Lys Gly Arg Gly Gly Lys Asn Leu Leu Leu Met Ser His Met Asp
                85                  90                  95

Thr Val Tyr Leu Lys Gly Ile Leu Ala Lys Ala Pro Phe Arg Val Glu
            100                 105                 110

Gly Asp Lys Ala Tyr Gly Pro Gly Ile Ala Asp Lys Gly Gly Asn
        115                 120                 125

Ala Val Ile Leu His Thr Leu Lys Leu Leu Lys Glu Tyr Gly Val Arg
130                 135                 140

Asp Tyr Gly Thr Ile Thr Val Leu Phe Asn Thr Asp Glu Glu Lys Gly
145                 150                 155                 160

Ser Phe Gly Ser Arg Asp Leu Ile Gln Glu Ala Lys Leu Ala Asp
                165                 170                 175

Tyr Val Leu Ser Phe Glu Pro Thr Ser Ala Gly Asp Glu Lys Leu Ser
            180                 185                 190

Leu Gly Thr Ser Gly Ile Ala Tyr Val Gln Val Asn Ile Thr Gly Lys
        195                 200                 205

Ala Ser His Ala Gly Ala Ala Pro Glu Leu Gly Val Asn Ala Leu Val
210                 215                 220

Glu Ala Ser Asp Leu Val Leu Arg Thr Met Asn Ile Asp Asp Lys Ala
225                 230                 235                 240

Lys Asn Leu Arg Phe Asn Trp Thr Ile Ala Lys Ala Gly Asn Val Ser
                245                 250                 255

Asn Ile Ile Pro Ala Ser Ala Thr Leu Asn Ala Asp Val Arg Tyr Ala
            260                 265                 270

Arg Asn Glu Asp Phe Asp Ala Ala Met Lys Thr Leu Glu Arg Ala
        275                 280                 285

Gln Gln Lys Lys Leu Pro Glu Ala Asp Val Lys Val Ile Val Thr Arg
290                 295                 300

Gly Arg Pro Ala Phe Asn Ala Gly Glu Gly Gly Lys Lys Leu Val Asp
305                 310                 315                 320

Lys Ala Val Ala Tyr Tyr Lys Glu Ala Gly Gly Thr Leu Gly Val Glu
                325                 330                 335

Glu Arg Thr Gly Gly Gly Thr Asp Ala Ala Tyr Ala Ala Leu Ser Gly
            340                 345                 350

Lys Pro Val Ile Glu Ser Leu Gly Leu Pro Gly Phe Gly Tyr His Ser
        355                 360                 365

Asp Lys Ala Glu Tyr Val Asp Ile Ser Ala Ile Pro Arg Arg Leu Tyr
370                 375                 380
```

```
Met Ala Ala Arg Leu Ile Met Asp Leu Gly Ala Gly Lys Glu Phe Leu
385                 390                 395                 400

Glu Ile Asp
```